(12) United States Patent
Schaffer et al.

(10) Patent No.: US 7,851,196 B2
(45) Date of Patent: *Dec. 14, 2010

(54) METHODS FOR PURIFYING ADENO-ASSOCIATED VIRUS PARTICLES

(75) Inventors: David V. Schaffer, Pleasant Hill, CA (US); Joshua N. Leonard, Silver Spring, MD (US)

(73) Assignee: The Regents of the University of California, Oakland, CA (US)

( * ) Notice: Subject to any disclaimer, the term of this patent is extended or adjusted under 35 U.S.C. 154(b) by 665 days.

This patent is subject to a terminal disclaimer.

(21) Appl. No.: 11/739,441

(22) Filed: Apr. 24, 2007

(65) Prior Publication Data

US 2007/0254352 A1    Nov. 1, 2007

Related U.S. Application Data

(60) Provisional application No. 60/796,911, filed on May 1, 2006.

(51) Int. Cl.
| | |
|---|---|
| *C12N 7/02* | (2006.01) |
| *C12N 7/00* | (2006.01) |
| *C12N 7/04* | (2006.01) |
| *C12N 15/00* | (2006.01) |
| *C12N 1/02* | (2006.01) |
| *C12N 13/00* | (2006.01) |
| *C12Q 1/70* | (2006.01) |
| *A01N 63/00* | (2006.01) |
| *A61K 39/00* | (2006.01) |
| *A61K 39/12* | (2006.01) |
| *A61K 39/235* | (2006.01) |
| *C07H 21/02* | (2006.01) |

(52) U.S. Cl. .................. 435/239; 435/235.1; 435/236; 435/261; 435/5; 435/173.9; 435/320.1; 424/184.1; 424/204.1; 424/233.1; 424/93.6; 536/23.1

(58) Field of Classification Search .................. None
See application file for complete search history.

(56) References Cited

U.S. PATENT DOCUMENTS 7,625,570 B1 * 12/2009 Schaffer et al. .......... 424/233.1

OTHER PUBLICATIONS

Leonard et al., Enhanced Preparation of Adeno-Associated Viral Vectors by Using High Hydrostatic Pressure to Selectively Inactivate Helper Adenovirus, 2007, Biotechnology and Bioengineering, vol. 97, No. 5, pp. 1170-1179.*
Pontes et al., "Pressure inactivation of animal viruses: potential biotechnological applications", *High Pressure Research in the Biosciences and Biotechnology*, H. K, Editor. 1997, p. 91-94.
Wilkinson et al., "Resistance of poliovirus to inactivation by high hydrostatic pressures", *Innovative Food Science and Emerging Technologies*. 2001. 2:95-98.

* cited by examiner

*Primary Examiner*—Zachariah Lucas
*Assistant Examiner*—Benjamin P Blumel
(74) *Attorney, Agent, or Firm*—Paula A. Borden; Bozicevic, Field & Francis LLP

(57) ABSTRACT

The present invention provides methods of purifying encapsidated virus, e.g., viral particles comprising viral nucleic acid, from compositions comprising encapsidated viral nucleic acid and viral particles that lack viral nucleic acid; methods for reducing the particle:genome ratio in a preparation of encapsidated viral nucleic acid; and methods for selectively inactivating viral particles that lack viral nucleic acid in a liquid composition comprising encapsidated viral nucleic acid and the viral particles that lack viral nucleic acid. The methods generally involve subjecting the composition to hydrostatic pressure such that the viral particles lacking viral nucleic acid are selectively inactivated.

24 Claims, No Drawings

METHODS FOR PURIFYING ADENO-ASSOCIATED VIRUS PARTICLES

BACKGROUND

Recombinant adeno-associated virus (AAV) is a highly promising gene therapy vector for numerous reasons, including its non-pathogenicity and its ability to induce long-term expression of a transgene in multiple target cell types. However, the large scale production of AAV is complex, either involving transient plasmid transfection or co-infection with a helper virus (such as adenovirus), which must eventually be removed from the product to avoid helper-induced pathogenicity. In addition, methods of generating recombinant AAV (rAAV) involving either helper plasmid or helper virus result in a mixture of encapsidated rAAV and AAV particles that lack viral nucleic acid (e.g., "empty shells"). Current methods for removing the empty shells include ultracentrifugation through a cesium chloride (CsCl) gradient. However, CsCl is toxic to mammals, and the CsCl gradient/ultracentrifugation method is not amenable to larger scale preparation. Furthermore, the cesium can inactivate viral particles that include viral genomes.

There is a need in the art for methods for selectively inactivating empty viral particles while leaving viral particles that contain viral genomes that are active and intact.

Literature

Pontes L, F. L., Giongo V, Araujo J R V, Sepulveda A, Vilas-Boas M, Bonafe C F S, Silva J L, *Pressure inactivation of animal viruses: potential biotechnological applications*, in High Pressure Research in the Biosciences and Biotechnology, H. K, Editor. 1997, Leuven University Press: Leuven. p. 91-94; Wilkinson N, Kurdziel A S, Langton S, Needs S, Cook N. Resistance of poliovirus to inactivation by high hydrostatic pressures. Innovative Food Science and Emerging Technologies. 2001. 2:95-98.

SUMMARY OF THE INVENTION

The present invention provides methods of purifying encapsidated virus, e.g., viral particles comprising viral nucleic acid, from compositions comprising encapsidated viral nucleic acid and viral particles that lack viral nucleic acid; methods for reducing the particle:genome ratio in a preparation of encapsidated viral nucleic acid; and methods for selectively inactivating viral particles that lack viral nucleic acid in a liquid composition comprising encapsidated viral nucleic acid and the viral particles that lack viral nucleic acid. The methods generally involve subjecting the composition to hydrostatic pressure such that the viral particles lacking viral nucleic acid are selectively inactivated.

DEFINITIONS

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

An "infectious" virus or viral particle is one that comprises a polynucleotide component which it is capable of delivering into a cell for which the viral species is trophic. The term does not necessarily imply any replication capacity of the virus. Assays for counting infectious viral particles are described elsewhere in this disclosure and in the art. Viral infectivity can be expressed as the P:I ratio, or the ratio of total viral particles to infective viral particles.

As used herein, the terms "viral genome" and "viral nucleic acid" are used interchangeably to refer to viral nucleic acid. The viral nucleic acid can be in any of various forms. For example, in the context of AAV, AAV nucleic acid includes rAAV, wild-type AAV, naturally-occurring AAV, and the like.

A "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per $10^8$ rAAV particles, less than about 1 rcAAV per $10^{12}$ rAAV particles, or no rcAAV).

"Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

As used herein, "pharmaceutically acceptable carrier" includes any material which, when combined with an active ingredient of a composition, allows the ingredient to retain biological activity and without causing disruptive physiological reactions, e.g., disruptive reactions with the subject's immune system. Examples include, but are not limited to, any of the standard pharmaceutical carriers such as a phosphate buffered saline solution, water, emulsions such as oil/water emulsion, and various types of wetting agents. Exemplary diluents for aerosol or parenteral administration are phosphate buffered saline or normal (0.9%) saline. Compositions comprising such carriers are formulated by well known conventional methods (see, for example, Remington's Pharmaceutical Sciences, Chapter 43, 14th Ed. or latest edition, Mack Publishing Co., Easton Pa. 18042, USA; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a viral particle" includes a plurality of such particles and reference to "the hydrostatic pressure treatment" includes reference to one or more hydrostatic pressure treatments and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides methods of purifying encapsidated virus, e.g., viral particles comprising viral nucleic acid, from compositions comprising encapsidated viral nucleic acid and viral particles that lack viral nucleic acid; methods for reducing the particle:genome ratio in a preparation of encapsidated viral nucleic acid; and methods for selectively inactivating viral particles that lack viral nucleic acid in a liquid composition comprising encapsidated viral nucleic acid and the viral particles that lack viral nucleic acid. The methods generally involve subjecting the composition to hydrostatic pressure such that the viral particles lacking viral nucleic acid are selectively inactivated.

The methods are useful for generating compositions that comprise active (infectious) AAV (e.g., AAV particles), e.g., viral particles comprising recombinant AAV (rAAV); and that have a reduced proportion of AAV viral particles that lack viral nucleic acid and which may be present in the composition before the hydrostatic pressure treatment. For convenience, the viral composition before being treated with a subject method is referred to herein as the "starting composition" or the "untreated composition"; and the viral composition after being treated with a subject method is referred to herein as the "treated composition" or the "hydrostatic pressure-treated composition." Exemplary, non-limiting rAAV particles include heterologous nucleic acids such as are discussed in, e.g., WO 2005/005610.

In some embodiments, subject methods involve subjecting a viral composition to high hydrostatic pressure, where the viral composition comprises: a) AAV viral particles comprising AAV nucleic acid; and (b) AAV viral particles lacking nucleic acid, including lacking AAV nucleic acid. Viral particles containing viral nucleic acid (e.g., AAV particles containing AAV nucleic acid) are also referred to herein as "full particles" or "full viral particles." Viral particles that lack nucleic acid (e.g., that lack viral nucleic acid) are also referred to herein as "empty shells" or "empty particles" or "empty viral particles." In many embodiments, the viral particles (both empty and full) are AAV viral particles, e.g., comprise AAV capsid protein(s). The method can also be applied to other encapsidated viruses.

A subject method results in selective inactivation of empty viral particles in a composition comprising empty viral particles and viral particles comprising AAV nucleic acid. In some embodiments, the effectiveness of the method is assessed by determining the particle to genome ratio, e.g., the ratio of viral particles (including empty particles and viral particles containing AAV nucleic acid) to viral nucleic acid ("viral genome"). In some embodiments, a subject method provides for a ratio of total viral particles to viral nucleic acid of less than about 50:1, less than about 25:1, less than about 10:1, less than about 5:1, or less than about 2:1, e.g., about 1:1. In other words, in some embodiments, a subject method provides for a ratio of total viral particles to viral nucleic acid that is in a range of from about 50:1 to about 2:1 or less, e.g., from about 50:1 to about 45:1, from about 45:1 to about 40:1, from about 40:1 to about 35:1, from about 35:1 to about 30:1, from about 30:1 to about 25:1, from about 25:1 to about 20:1, from about 20:1 to about 15:1, from about 15:1 to about 10:1, from about 10:1 to about 5:1, or from about 5:1 to about 2:1, or less than 2:1, e.g., about 1:1.

A subject method is effective to reduce the proportion of empty viral particles in a viral composition to less than about 50%, less than about 45%, less than about 40%, less than about 35%, less than about 30%, less than about 25%, less than about 20%, less than about 15%, less than about 10%, less than about 5%, or less than about 2%, of the total viral particles, where "total viral particles" includes viral particles comprising viral nucleic acid and viral particles lacking viral nucleic acid (e.g., empty particles plus full particles).

Viral particles containing viral nucleic acid retain activity, e.g., infectivity. A subject method results in a composition of viral particles comprising viral nucleic acid, where the infectivity of viral particles comprising viral nucleic acid present in the treated composition is at least about 70%, at least about 80%, at least about 90%, at least about 95%, at least about 98%, or at least about 99%, or 100% of the pre-treatment infectivity, e.g., the infectivity of viral particles comprising viral nucleic acid present in the untreated composition.

A subject method is effective to inactivate at least about 50%, at least about 60%, at least about 65%, at least about 70%, at least about 75%, at least about 80%, at least about 85%, at least about 90%, or at least about 95%, or more, of the viral particles that lack viral nucleic acid and that are present in the untreated composition are inactivated.

"Inactivation of viral particles lacking viral nucleic acid" (also referred to as "destruction of viral particles lacking viral nucleic acid") refers to one or more of: irreversible collapsing of the empty particles; dissociation of the empty particles; and bursting of the empty particles. In some embodiments, an inactivated viral particle is not recognized or bound by an antibody specific for an AAV capsid protein.

A subject method involves subjecting a viral composition comprising a) viral particles comprising viral nucleic acid (e.g., AAV particles comprising AAV nucleic acid); and (b) viral particles lacking viral nucleic acid (e.g., AAV particles lacking nucleic acid, including lacking AAV nucleic acid) to a hydrostatic pressure at a pressure and for a time such that the viral particles lacking viral nucleic acid are selectively inactivated. In some embodiments, the starting viral composition is subjected to a pressure in a range of from about 200 megapascal (MPa) to about 1000 MPa, e.g., in a range of from about 200 MPa to about 250 MPa, from about 250 MPa to about 300 MPa, from about 300 MPa to about 350 MPa, from about 350 MPa to about 400 MPa, from about 400 MPa to about 450 MPa, from about 450 MPa to about 500 MPa, from about 500 MPa to about 600 MPa, from about 600 MPa to about 700 MPa, from about 700 MPa to about 800 MPa, from about 800 MPa to about 900 MPa, or from about 900 MPa to about 1000 MPa, for a time such that at least about 50%, at least about 60%, at least about 65%, at least about 70%, at least about 75%, at least about 80%, at least about 85%, at least about 90%, or at least about 95%, or more, of the viral particles lacking viral nucleic acid are inactivated.

Suitable time periods for achieving selective inactivation of empty viral particles present in the starting viral composition range from about 1 minute to about 3 hours, e.g., from about 1 minute to about 5 minutes, from about 5 minutes to about 10 minutes, from about 10 minutes to about 15 minutes, from about 15 minutes to about 20 minutes, from about 20 minutes to about 30 minutes, from about 30 minutes to about 45 minutes, from about 45 minutes to about 60 minutes, from about 60 minutes to about 90 minutes, from about 90 minutes to about 120 minutes, or from about 120 minutes to about 180 minutes.

In many embodiments, the temperature of composition is held relatively constant during treatment with hydrostatic pressure, e.g., the temperature of the composition does not fluctuate by more than about 1° C., by more than about 2° C., by more than about 3° C., by more than about 4° C., by more than about 5° C., by more than about 10° C., by more than about 15° C., or by more than about 20° C. In some embodiments, the temperature of the composition is held at or below about 40° C., e.g., the temperature of the composition is maintained at a relatively constant temperature in the range of from about 4° C. to about 40° C., e.g., from about 4° C. to about 5° C., from about 5° C. to about 7° C., from about 7° C. to about 10° C., from about 10° C. to about 15° C., from about 15° C. to about 20° C., from about 20° C. to about 25° C., from about 25° C. to about 30° C., from about 30° C. to about 35° C., or from about 35° C. to about 40° C.

In some embodiments, the starting composition is treated with multiple rounds of hydrostatic pressure. In some embodiments, the starting composition is treated with multiple rounds of alternating high hydrostatic pressure and low hydrostatic pressure. For example, in some embodiments, a subject method comprises: a) treating a starting viral composition with a first pressure of from about 200 MPa to about 1000 MPa for about 1 minute to about 3 hours, as described above, generating a first pressure-treated viral composition; (b) treating the first pressure-treated viral composition with a second pressure in a range of from about 0 MPa to about 200 MPa for a period of time ranging from about 1 minute to about 60 minutes, generating a second pressure-treated viral composition; and (e) treating the second pressure-treated viral composition with a third pressure of from about 200 MPa to about 1000 MPa for about 1 minute to about 3 hours, as described above. In some embodiments, steps (b) and (c) are repeated one or more times, e.g., 1 time, 2 times, 3 times, 4 times, 5 times, 6 times, or more than 6 times.

The following are non-limiting examples of suitable protocols involving multiple rounds of high and low pressure. In some embodiments, a viral composition is subjected to a pressure treatment comprising: a) treating a viral composition with a first pressure in a range of from about 400 MPa to about 450 MPa for a time period of from about 1 minute to about 60 minutes, or from about 1 minute to about 30 minutes, or from about 1 minute to about 15 minutes, or from about 10 minutes to about 15 minutes, or from about 5 minutes to about 30 minutes, or from about 10 minutes to about 30 minutes, or from about 15 minutes to about 30 minutes, generating a first pressure-treated viral composition; b) treating the first pressure-treated viral composition with a second pressure in a range of from about 0 MPa to about 200 MPa for a time period of from about 1 minute to about 60 minutes, or from about 1 minute to about 30 minutes, or from about 1 minute to about 15 minutes, or from about 10 minutes to about 15 minutes, or from about 5 minutes to about 30 minutes, or from about 10 minutes to about 30 minutes, or from about 15 minutes to about 30 minutes, generating a second pressure-treated viral composition; and c) treating the second pressure-treated viral composition with a third pressure of in a range of from about 400 MPa to about 450 MPa for a time period of from about 1 minute to about 60 minutes, or from about 1 minute to about 30 minutes, or from about 1 minute to about 15 minutes, or from about 10 minutes to about 15 minutes, or from about 5 minutes to about 30 minutes, or from about 10 minutes to about 30 minutes, or from about 15 minutes to about 30 minutes, generating a third pressure-treated viral composition. In some embodiments, this exemplary method further comprises repeating steps (b) and (c) at least one time, at least 2 times, at least 3 times, at least 4 times, or at least 5 times.

In some embodiments, the rate at which the hydrostatic pressure on the viral composition is increased and/or decreased varies from about 1 MPa/second (1 MPa/s) to about 20 MPa/s, e.g., from about 1 MPa/s to about 2 MPa/s, from about 2 MPa/s to about 3 MPa/s, from about 3 MPa/s to about 4 MPa/s, from about 4 MPa/s to about 5 MPa/s, from about 5 MPa/s to about 7 MPa/s, from about 7 to about 10 MPa/s, from about 10 MPa/s to about 12 MPa/s, from about 12 MPa/s to about 15 MPa/s, from about 15 MPa/s to about 18 MPa/s, or from about 18 MPa/s to about 20 MPa/s.

The salt concentration of the viral composition being treated with a subject method will range from about 0 mM to about 5 M, e.g., from about 0 mM to about 0.5 mM, from about 0.5 mM to about 1 mM, from about 1 mM to about 5 mM, from about 5 mM to about 150 mM, e.g., from about 5 mM to about 10 mM, from about 10 mM to about 25 mM, from about 25 mM to about 50 mM, from about 50 mM to about 75 mM, from about 75 mM to about 100 mM, from about 100 mM to about 125 mM, from about 125 mM to about 150 mM, from about 150 mM to about 250 mM, from about 250 mM to about 500 mM, from about 500 mM to about 750 mM, from about 750 mM to about 1 M, from about 1 M to about 1.5 M, from about 1.5 M to about 2 M, from about 2 M to about 2.5 M, from about 2 M to about 3 M, from about 3 M to about 3.5 M, from about 3.5 M to about 4 M, from about 4 M to about 4.5 M, or from about 4.5 M to about 5 M. Suitable salts include, but are not limited to, NaCl, $MgCl_2$, KCl, $ZnCl_2$, etc., and mixtures thereof.

In general, the higher the hydrostatic pressure with which the viral composition is treated, the shorter the time required to selectively inactivate empty viral particles which may be present in the untreated viral composition. The following are exemplary, non-limiting embodiments of the subject treatment method.

In some embodiments, a viral composition is subjected to a pressure in a range of from about 200 MPa to about 500 MPa for a time such that empty viral particles are selectively inactivated. In some of these embodiments, the viral composition is subjected to a pressure in a range of from about 200 MPa to about 500 MPa for a time period of from about 1 minute to about 3 hours. In some embodiments, the viral composition is subjected to a pressure in a range of from about 200 MPa to about 250 MPa for a time period of from about 2 hours to about 3 hours. In some embodiments, the viral composition is subjected to a pressure in a range of from about 250 MPa to about 300 MPa for a time period of from about 30 minutes to about 2 hours, or from about 30 minutes to about 60 minutes. In some embodiments, the viral composition is subjected to a pressure in a range of from about 300 MPa to about 350 MPa for a time period of from about 30 minutes to about 60 minutes, or from about 15 minutes to about 60 minutes, or from about 15 minutes to about 45 minutes, or from about 15 minutes to about 30 minutes. In some embodiments, the viral composition is subjected to a pressure in a range of from about 350 MPa to about 400 MPa for a time period of from about 1 minute to about 60 minutes, or from about 1 minute to about 30 minutes, or from about 1 minute to about 15 minutes, or from about 10 minutes to about 15 minutes, or from about 5 minutes to about 30 minutes, or from about 10 minutes to about 30 minutes, or from about 15 minutes to about 30 minutes. In some embodiments, the viral composition is subjected to a pressure in a range of from about 400 MPa to about 450 MPa for a time period of from about 1 minute to about 60 minutes, or from about 1 minute to about 30 minutes, or from about 1 minute to about 15 minutes, or from about 10 minutes to about 15 minutes, or from about 5 minutes to about 30 minutes, or from about 10 minutes to about 30 minutes, or from about 15 minutes to about 30 minutes. In some embodiments, the viral composition is subjected to a pressure in a range of from about 450 MPa to about 500 MPa for a time period of from about 1 minute to about 60 minutes, or from about 1 minute to about 30 minutes, or from about 1 minute to about 15 minutes, or from about 10 minutes to about 15 minutes, or from about 5 minutes to about 30 minutes, or from about 10 minutes to about 30 minutes, or from about 15 minutes to about 30 minutes.

An external pressure source is used for supplying pressure to the pressure chamber of the vessel containing the viral composition. According to Pascal's Law, this hydrostatic pressure has a uniform effect on all materials inside the pressure vessel. Any known device that provides for a pressure of up to about 500 MPa or greater (e.g., up to about 1000 MPa) is suitable for use in carrying out a subject method. See, e.g., Cléry-Barraud et al. (2004) Appl Environ Microbiol. 70(1): 635-637; and high hydrostatic pressure systems available from Avure Technologies (Kent, Wash.).

An untreated "starting" viral composition (a viral composition that has not been treated with hydrostatic pressure according to the instant invention) comprises a viral particle comprising viral nucleic acid (e.g., an AAV particle comprising AAV, an AAV particle comprising rAAV, etc.) and a viral particle lacking viral nucleic acid (e.g., an AAV particle lacking nucleic acid, including lacking AAV nucleic acid). In many embodiments, the starting (non-pressure-treated) viral composition is a cell-free viral composition. In some embodiments, the starting viral composition is free of cellular proteins and/or other contaminants. In other embodiments, the starting viral composition is a crude cell lysated. The starting viral composition may comprise one or more additional components, where such components may be one or more of: a buffer (e.g., a phosphate buffer, a Tris buffer, etc.); a salt (e.g., NaCl, $MgCl_2$, KCl, etc.); ions, e.g., magnesium ions, manganese ions, zinc ions, etc.); a preservative; a solubilizing agent; a detergent, e.g., a non-ionic detergent; dimethylsulfoxide; and the like.

In some embodiments, one or more ion exchange chromatographic procedures and/or affinity chromatographic procedures are carried out on the viral composition before or after a subject hydrostatic pressure treatment. See, e.g., U.S. Pat. No. 6,566,118. For example, opposing ion exchange chromatography steps may be applied in any order, and may include additional opposing ion exchange chromatography step(s). For example, in some embodiments, a lysate or culture supernatant is subjected to cation exchange chromatography followed by anion exchange chromatography followed by cation exchange chromatography. In some embodiments, heparin sulfate is used in at least one (e.g., the last) cation exchange chromatography step.

For example, a clarified AAV lysate can be loaded on an positively charged anion-exchange column, such as an N-charged amino or imino resin (e.g. POROS 50 PI, or any DEAE, TMAE, tertiary or quaternary amine, or PEI-based resin) or a negatively charged cation-exchange column (such as HS, SP, CM or any sulfo-, phospho- or carboxy-based cationic resin). The column can be washed with a buffer (such as chromatography buffer A/TMEG). The column can be eluted with a gradient of increasing NaCl concentration and fractions can be collected and assayed for the presence of AAV and/or contaminants.

Other procedures can be used in place of, or in addition to, the above-described anion and cation exchange procedures, based on inter-molecular associations mediated by features other than charge as is known in the art. Such other procedures include intermolecular associations based on ligand-receptor pairs (such as antibody-antigen or lectin-carbohydrate interactions), as well as separations based on other attributes of the molecules, such as molecular sieving chromatography based on size and/or shape. As one non-limiting example, the filtrate, crude cell lysate, or partially purified AAV preparation may be loaded on a column that contains an AAV-specific antibody (e.g., antibody specific for AAV capsid protein(s)). This column can bind AAV particles. The column can be rinsed with buffer to remove contaminating proteins, and then eluted with a gradient or step of increasing NaCl concentration and fractions can be collected. Alternatively, such a column can be eluted with a buffer of different pH than that of the loading buffer. As one non-limiting example, the filtrate, crude cell lysate, or partially purified AAV preparation may be loaded on a heparin column. Optional wash steps may precede elution from the heparin column.

A viral preparation (e.g., a viral preparation that has been subjected to affinity chromatography, as described above) can be injected on a positively charged anion-exchange column and/or a negatively charged cation-exchange column (such as those referred to above). The column can be washed with a buffer (such as chromatography buffer A/TMEG). The column can be eluted with a gradient of increasing NaCl concentration and fractions can be collected.

The of AAV-containing fractions eluted from an anion exchange column as described above can be concentrated and purified by tangential flow filtration (TFF), for example in a Filtron Ultrasette or Millipore Pellicon unit. A membrane of suitable molecular weight cut-off (such as a 100,000 or 300,000 cut-off), is typically composed of a polymer such as regenerated cellulose or polyethersulfone. The preparation is filtered through the membrane, and the product is retained. The retained material can be diafiltered using the membrane with successive washes of a suitable buffer such as Ringer's Balanced Salt Solution+5% glycerol. The final sample is highly enriched for the product and can be sterile filtered through a 0.2µ filter and stored for use.

In the purification and concentration of AAV with tangential flow filtration from post-anionic exchange column material, the 300,000 molecular weight cut-off membrane has resulted in higher yields of replicative units than the 100,000 molecular weight cut-off membrane.

In some embodiments, lysate or culture supernatant is subjected to filtration (such as depth filtration) to clarify the lysate, followed by heat killing, followed by filtration (such as filtration using a 0.5 µm filter) to further clarify the lysate, followed by cation exchange chromatography (using, for example, an MS resin), followed by nuclease digestion, followed by anion exchange chromatography (using, for example, a PI resin), followed by heparin sulfate chromatography, followed by gel filtration.

Inactivation of viral particles lacking viral nucleic acid provides a means to distinguish between empty viral particles and viral particles containing viral nucleic acid. Thus, in some embodiments, a viral composition comprising empty viral particles and viral particles containing AAV (e.g. rAAV) is first subjected to hydrostatic pressure according to the instant invention, generating a hydrostatic pressure-treated viral composition; and the hydrostatic pressure-treated viral composition is further subjected to one or more additional purification steps. For example, in some embodiments, the hydrostatic pressure-treated viral composition is subjected to affinity chromatography on a heparin column. In other embodiments, the hydrostatic pressure-treated viral composition is subjected to affinity chromatography, where an antibody specific for AAV capsid protein(s) is immobilized on a solid support. In other embodiments, the hydrostatic pressure-treated viral composition is subjected to anion exchange chromatography. In other embodiments, the hydrostatic pressure-treated viral composition is subjected to cation exchange chromatography. In other embodiments, the hydrostatic pressure-treated viral composition is subjected to anion exchange chromatography and affinity chromatography, in either order. In other embodiments, the hydrostatic pressure-treated viral composition is subjected to cation exchange chromatography and affinity chromatography, in either order.

Compositions

The present invention further provides a viral composition, including a pharmaceutical composition, which is produced using a subject method, where the viral composition comprises active AAV particles and less than about 40%, less than about 30%, less than about 25%, less than about 20%, less than about 15%, less than about 10%, less than about 5%, or less than about 2% empty particles. A subject viral composition will in some embodiments comprise active AAV; and will in some embodiments include one or more of: a buffer (e.g., a phosphate buffer, a Tris buffer, etc.); a salt (e.g., NaCl, $MgCl_2$, etc.); ions, e.g., magnesium ions, manganese ions, zinc ions, etc.); a preservative; a solubilizing agent; a detergent, e.g., a non-ionic detergent; dimethylsulfoxide; and the like. In some embodiments, a subject composition, including a subject pharmaceutical composition, will comprise an amount of from about $10^6$ to about $10^{15}$ of the rAAV virions, e.g., from about $10^8$ to about $10^{12}$ rAAV virions per unit dosage form, e.g., per ml, per 0.5 ml, etc.

In some embodiments, a subject viral composition is a pharmaceutical composition, comprising a pharmaceutically acceptable excipient. In some instances, the composition can comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", $19^{th}$ Ed. (1995) Mack Publishing Co.; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or see, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Treatment of Viral Compositions with Hydrostatic Pressure

After treating samples at 0 MPa (control) or at 450 MPa (near the maximum pressure at which AAV2 can be treated without losing activity), images of the AAV2 vector particles were obtained using transmission electron microscopy (TEM). The samples were negatively stained with uranyl acetate, which makes it possible to identify viral particles and to discriminate full particles from empty particles (which do not contain viral DNA). TEM images revealed that a pressure treatment at 450 MPa for 15 minutes enriches the viral prep for full particles, but it does not completely eliminate the empty particles. The data, shown in Table 1, are summarized as follows: the control sample has 55% full (N=65), whereas the 450 MPa treated sample has 72% full (N=29).

TABLE 1

| Pressure | # full particles | # empty particles | % full particles |
|---|---|---|---|
| 0 MPa | 6 | 5 | 55% |
| 0 MPa | 14 | 15 | 48% |
| 0 MPa | 14 | 7 | 67% |
| 0 MPa | 2 | 2 | 50% |
| 450 MPa | 7 | 1 | 88% |
| 450 MPa | 6 | 4 | 60% |
| 450 MPa | 4 | 1 | 80% |
| 450 MPa | 1 | 0 | 100% |
| 450 MPa | 3 | 2 | 60% |

From the above data, it was concluded that empty particles were preferentially destroyed under these conditions.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for selectively inactivating adeno-associated virus (AAV) viral particles lacking nucleic acid in a liquid viral composition comprising AAV viral particles comprising AAV nucleic acid and AAV viral particles lacking nucleic acid,
   the method comprising subjecting the liquid viral composition to a hydrostatic pressure at a pressure in a range of from about 200 MPa to about 500 MPa for a time period of from about 1 minute to about 3 hours, wherein said subjecting selectively inactivates AAV viral particles lacking nucleic acid.

2. The method of claim 1, wherein the composition is subjected to a pressure of at least about 350 MPa for a time of from about one hour to about 2 hours.

3. The method of claim 1, wherein the composition is subjected to a pressure of at least about 450 MPa for a time of from about 1 minute to about 30 minutes.

4. The method of claim 1, wherein the pressure is applied at a rate of from about 1 MPa/second (MPa/s) to about 20 MPa/s.

5. The method of claim 1, wherein the salt concentration of the viral composition is in a range of from about 0 mM to about 5 M.

6. The method of claim 5, wherein the salt concentration of the viral composition is in a range of from about 0.5 mM to about 5 M.

7. The method of claim 5, wherein the salt concentration of the viral composition is in a range of from about 10 mM to about 2 M.

8. The method of claim 1, wherein the composition is maintained at a temperature of less than about 40° C. during said subjecting.

9. The method of claim 1, wherein the composition is maintained at a temperature of less than about 37° C. during said subjecting.

10. The method of claim 1, wherein the composition is maintained at a temperature of less than about 35° C. during said subjecting.

11. The method of claim 1, wherein said subjecting results in inactivation of at least about 50% of the AAV viral particles lacking nucleic acid.

12. The method of claim 1, wherein said subjecting results in inactivation of at least about 70% of the AAV viral particles lacking nucleic acid.

13. The method of claim 1, wherein said subjecting results in inactivation of at least about 90% of the AAV viral particles lacking nucleic acid.

14. The method of claim 1, wherein the AAV viral particles are AAV serotype 2.

15. The method of claim 1, wherein the AAV nucleic acid is recombinant.

16. The method of claim 1, wherein the viral particles comprising AAV nucleic acid retain at least about 80% infectivity following subjecting the composition to hydrostatic pressure.

17. The method of claim 1, wherein said subjecting results in a viral composition in which the ratio of total viral particles to AAV nucleic acid is less than about 50:1.

18. The method of claim 1, wherein said subjecting results in a viral composition in which the ratio of total viral particles to AAV nucleic acid is less than about 25:1.

19. The method of claim 1, wherein said subjecting results in a viral composition in which the ratio of total viral particles to AAV nucleic acid is less than about 10:1.

20. The method of claim 1, wherein said subjecting results in a viral composition in which the ratio of total viral particles to AAV nucleic acid is less than about 5:1.

21. The method of claim 1, wherein said subjecting results in a viral composition in which the ratio of total viral particles to AAV nucleic acid is less than about 2:1.

22. The method of claim 1, wherein said subjecting results in a viral composition in which the ratio of total viral particles to AAV nucleic acid is about 1:1.

23. A method for selectively inactivating adeno-associated virus (AAV) viral particles lacking nucleic acid in a liquid viral composition comprising AAV viral particles comprising AAV nucleic acid and AAV viral particles lacking nucleic acid, the method comprising:
   a) treating the liquid viral composition with a first pressure in a range of from about 200 MPa to about 500 MPa for a period of time ranging from about 1 minute to about 60 minutes, generating a first pressure-treated viral composition;
   b) treating the first pressure-treated viral composition with a second pressure in a range of from about 0 MPa to about 200 MPa for a period of time ranging from about 1 minute to about 60 minutes, generating a second pressure-treated viral composition; and
   c) treating the second pressure-treated viral composition with a third pressure in a range of from about 200 MPa to about 500 MPa for a period of time ranging from about 1 minute to about 60 minutes, generating a third pressure-treated viral composition
   wherein said treating selectively inactivates AAV viral particles lacking nucleic acid.

24. The method of claim 23, further comprising repeating steps (b) and (c).

* * * * *